(12) United States Patent
Geigenberger et al.

(10) Patent No.: US 7,807,870 B2
(45) Date of Patent: Oct. 5, 2010

(54) METHOD FOR ALTERING THE CONTENT OF RESERVE SUBSTANCES IN PLANTS

(75) Inventors: Peter Geigenberger, Berlin (DE); Anke Langer, Potsdam (DE); Helene Vigeolas, Potsdam (DE); Marc Stitt Nigel, Potsdam (DE); Joost Thomas van Dongen, Potsdam (DE); Michael Udvardi, Golm (DE)

(73) Assignee: Max-Planck-Gesellschaft, Munich (DE)

( * ) Notice: Subject to any disclaimer, the term of this patent is extended or adjusted under 35 U.S.C. 154(b) by 0 days.

(21) Appl. No.: 10/540,063

(22) PCT Filed: Dec. 23, 2003

(86) PCT No.: PCT/EP03/14774

§ 371 (c)(1),
(2), (4) Date: Jun. 22, 2005

(87) PCT Pub. No.: WO2004/057946

PCT Pub. Date: Jul. 15, 2004

(65) Prior Publication Data

US 2006/0053515 A1    Mar. 9, 2006

(30) Foreign Application Priority Data

Dec. 23, 2002    (DE) ............... 102 60 707

(51) Int. Cl.
*C12N 15/83* (2006.01)
*C12N 15/11* (2006.01)
*C12N 15/00* (2006.01)

(52) U.S. Cl. ............... 800/284; 800/278; 800/281; 435/320.1; 435/468; 536/23.1; 536/23.6; 536/23.2

(58) Field of Classification Search ............... 435/69.1, 435/320.1, 468; 530/370; 800/278, 295, 800/320.2; 536/23.6
See application file for complete search history.

(56) References Cited

U.S. PATENT DOCUMENTS

| 5,925,805 A | * | 7/1999 | Ohlrogge et al. ............ 800/295 |
| 6,051,755 A | * | 4/2000 | Zou et al. .................... 800/281 |
| 6,174,724 B1 | * | 1/2001 | Rogers et al. ............... 435/419 |
| 6,232,526 B1 | * | 5/2001 | McElroy et al. ............. 800/278 |
| 6,372,961 B1 | | 4/2002 | Tarczynski et al. |
| 6,395,964 B1 | * | 5/2002 | Arntzen et al. .............. 800/288 |
| 6,552,250 B1 | * | 4/2003 | Nykiforuk et al. .......... 800/281 |
| 2002/0160378 A1 | * | 10/2002 | Harper et al. .................. 435/6 |

FOREIGN PATENT DOCUMENTS

| WO | WO-98/12913 | 4/1998 |
| WO | WO-99/02687 | 1/1999 |
| WO | WO-2004/087755 | 10/2004 |

OTHER PUBLICATIONS

Harper et al., Published Applications_NA_Main Database, 2002 0160378-US, published Oct. 31, 2002.*
Sowa (1998) PNAS 95: 10317-10321.*
Trevaskis et al., Two hemoglobin genes in *Arabidopsis thaliana*: the evolutionary origins of leghemoglobins. Proc Natl Acad Sci U S A. Oct. 28, 1997;94(22):12230-4.*
Broun et al (1988, Science 282:1315-1317.*
Lazar et al (1988, Mol. Cell Biol. 8:1247-1252.*
Doerks Tig 14, No. 6: 248-250, Jun. 1998.*
Trevaskis, B. et al., "Two Hemoglobin Genes in *Arabidopsis thaliana*: The Evolutionary Origins of Leghemoglobins." Database EMBL Accession No. U94999, Nov. 6, 1997.
Uchiumi, T. et al., "Genomic Leghemoglobin Genes of *Lotus japonicus*." Database EMBL Accession No. AB042718, Nov. 18, 2000.
Trevaskis, B. et al., "Two Hemoglobin Genes in *Arabidopsis thaliana*: The Evolutionary Origins of Leghemoglobins." Proc. Natl. Acad. Sci. USA 94 (1997), pp. 12230-12234.
Stougaard, J. et al., "Expression of a Complete Soybean Leghemoglobin Gene in Root Nodules of Transgenic *Lotus comiculatus*." Proc. Natl. Acad. Sci. USA 84 (1987), pp. 5754-5757.
Barata, R. et al., "Targeting of the Soybean Leghemoglobin to Tobacco Chloroplasts: Effects on Aerobic Metabolism in Transgenic Plants." Plant Science 155 (2000), pp. 193-202.

* cited by examiner

*Primary Examiner*—Anne Marie Grunberg
*Assistant Examiner*—Brent Page
(74) *Attorney, Agent, or Firm*—Connolly Bove Lodge & Hutz, LLP

(57) ABSTRACT

The invention relates to a method for modifying the storage reserve content in plants, where leghemoglobin- and/or hemoglobin-expressing transformed plants are employed, to corresponding plants, and to their use.

31 Claims, 6 Drawing Sheets

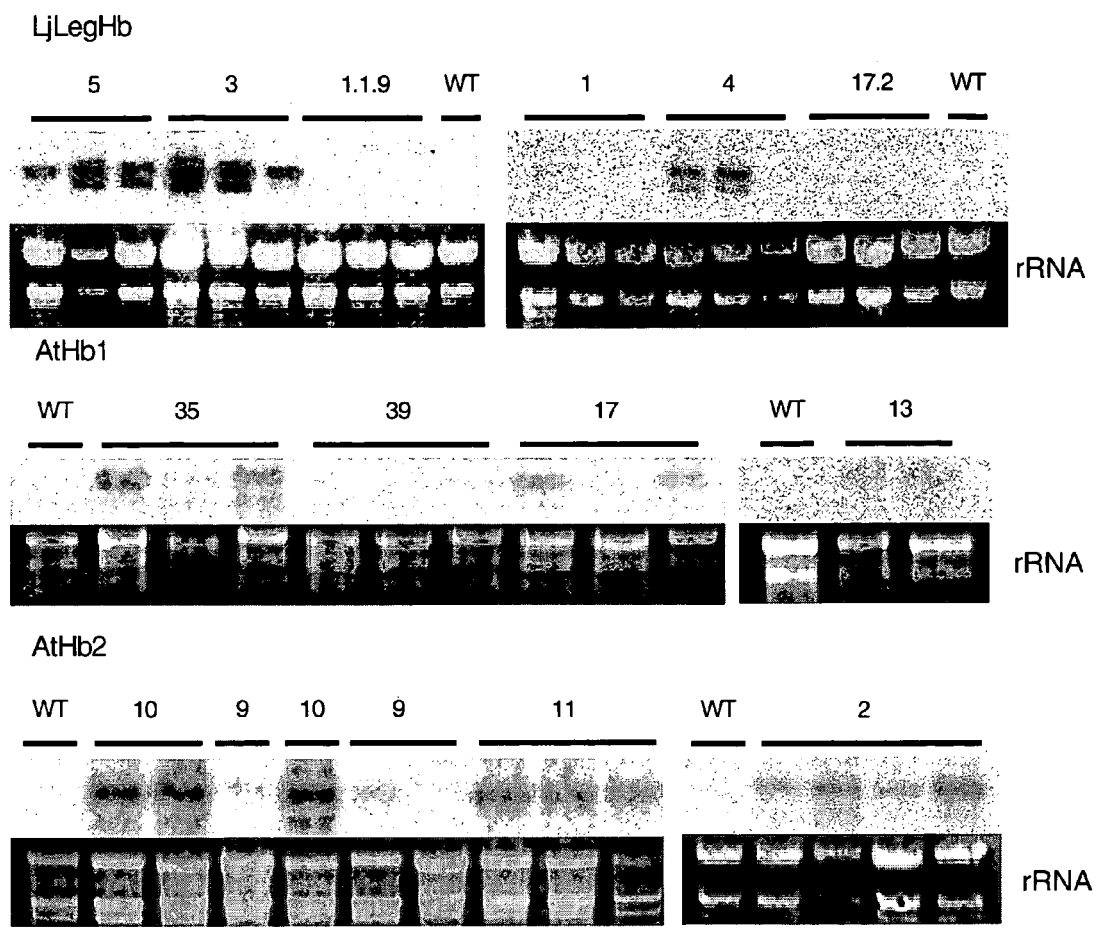
Figure 1. Northern Blot analyses with maturing seeds of transgenic Arabidopsis plants which have been transformed with Lotus leghemoglobin (LjLegHb), Arabidopsis Hemoglobin 1 (AtHb1) or Arabidopsis Hemoglobin 2 (AtHb2). The amount of the total RNA employed was determined by comparing the amount of ribosomal RNA (rRNA).

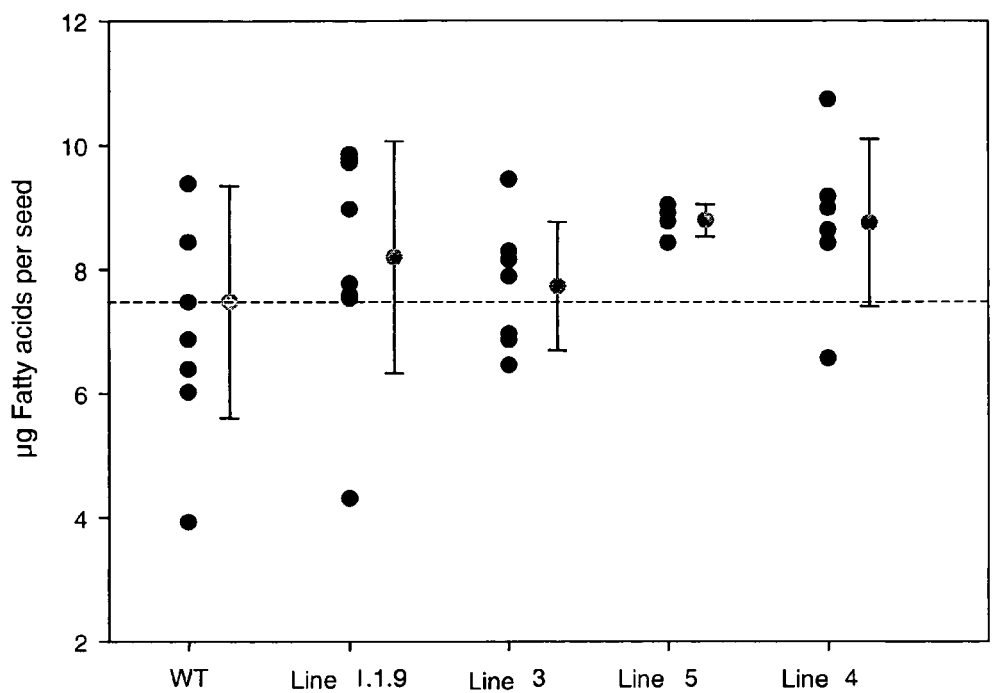
Figure 2. Graphic representation of the oil contents in T2 seeds of transgenic Arabidopsis lines which express LjLegHb in comparison with the control. The data from 4-9 individual measurements on in each case 5-10 seeds (●) and the resulting means with the corresponding standard deviations (◉) are shown.

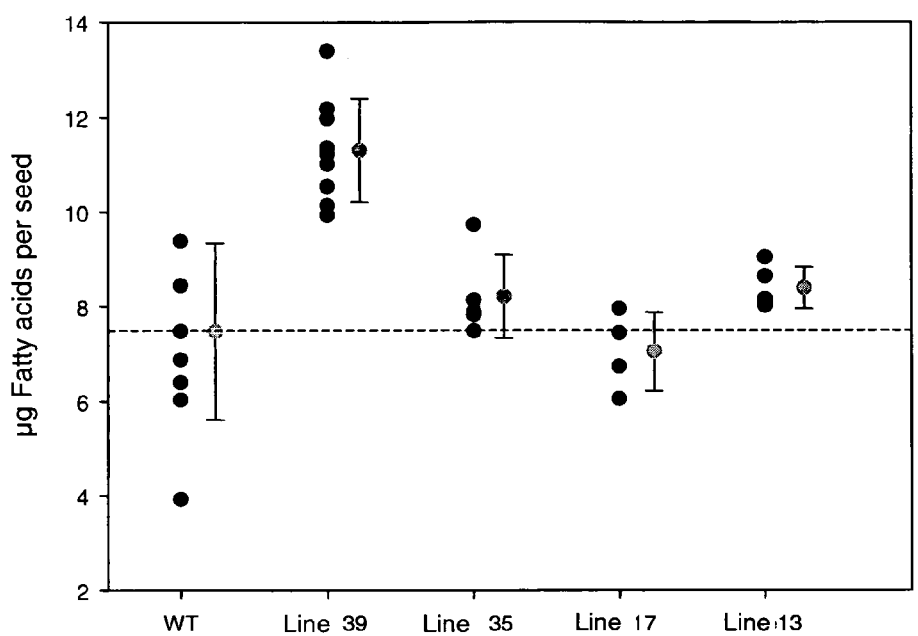
Figure 3. Graphic representation of the oil contents in T2 seeds of transgenic Arabidopsis lines which express AtHb1 in comparison with the control. The data from 4-9 individual measurements on in each case 5-10 seeds (●) and the resulting means with the corresponding standard deviations (◉) are shown.

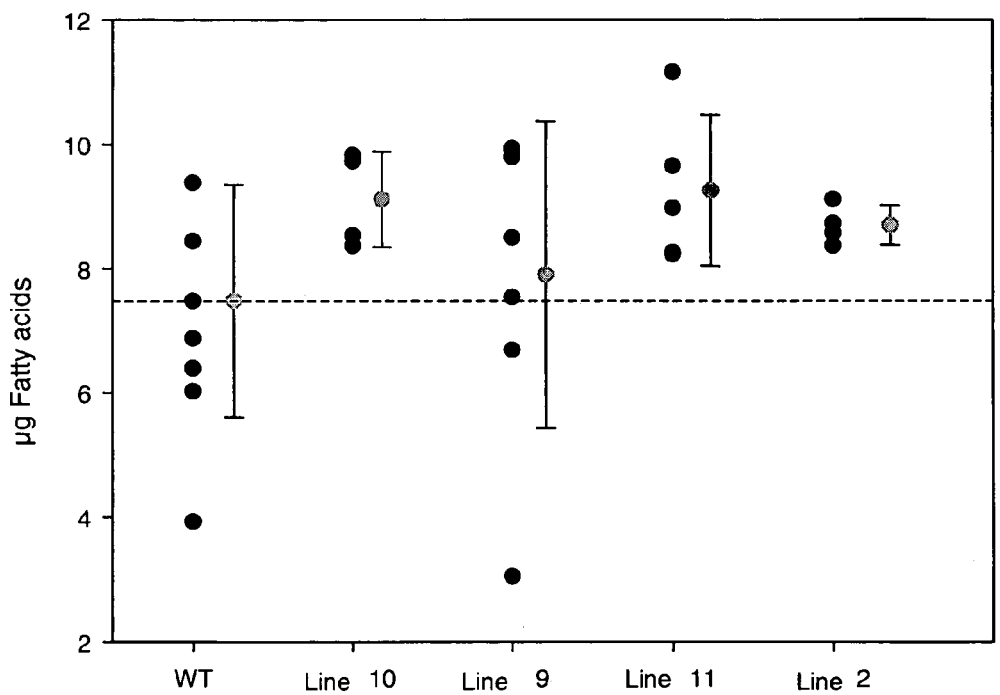
Figure 4. Graphic representation of the oil contents in T2 seeds of transgenic Arabidopsis lines which express AtHb2 in comparison with the control. The data from 4-9 individual measurements on in each case 5-10 seeds (●) and the resulting means with the corresponding standard deviations (◌) are shown.

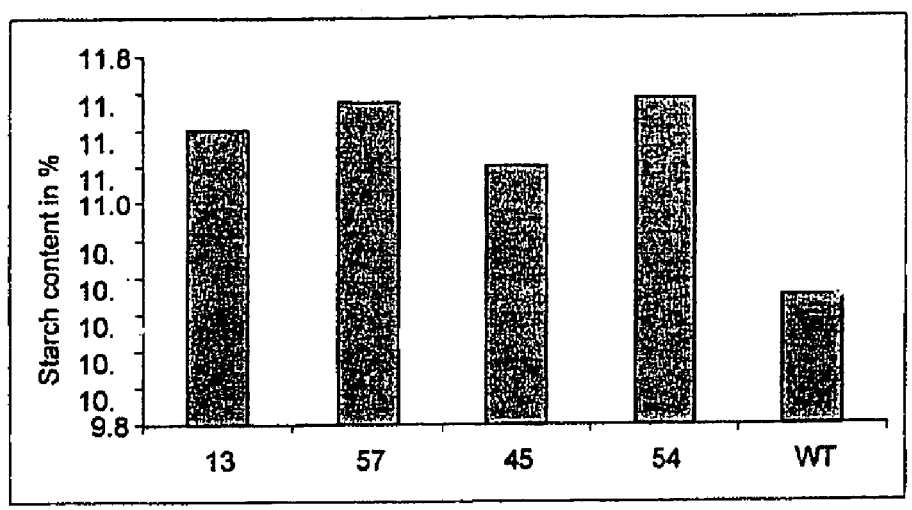

Figure 5. Starch content of leghemoglobin-expressing potato tubers in comparison with the wild type. Plants were grown in the polyhouse in Golm in summer 2003, and mature tubers were harvested. The starch content was measured by determining the specific gravity of the tubers. The data are based on in each case 334 tubers (line 13), 358 tubers (line 57), 380 tubers (line 45), 384 tubers (line 54) and 151 tubers (wild type).

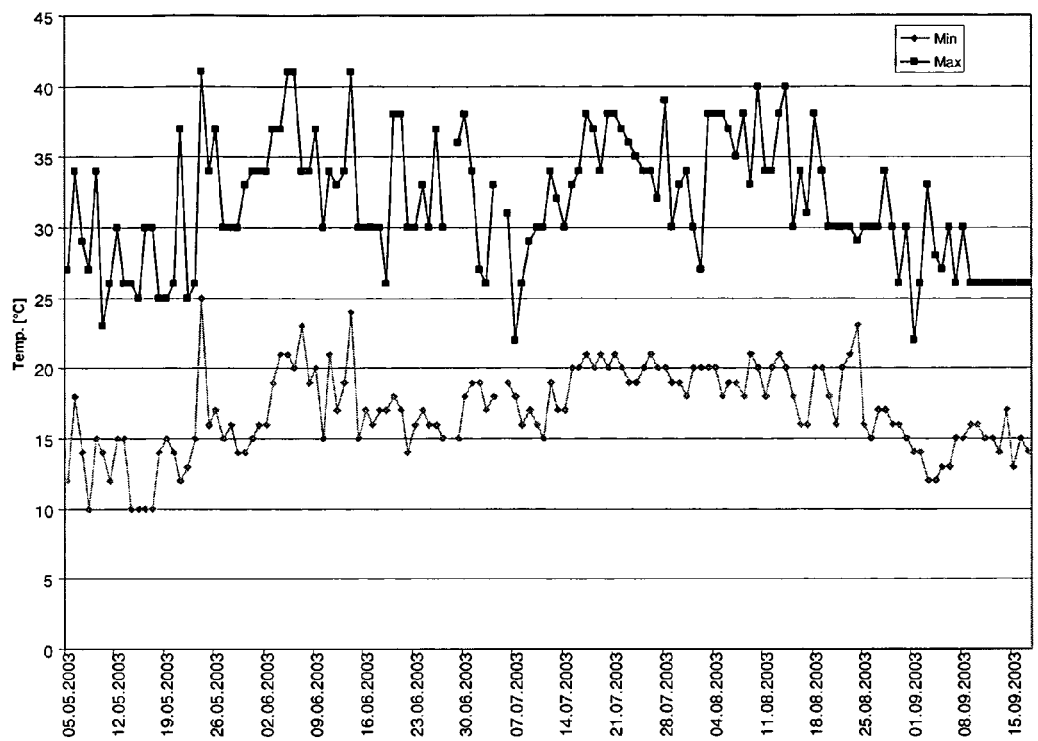
Figure 6. Temperature measurements in the polyhouse in which the transgenic potato plants which overexpressed the Lotus japonicus leghemoglobin were grown. The respective maximum and minimum temperatures are shown.

SEQUENCE LISTING

<160> NUMBER OF SEQ ID NOS: 6

<210> SEQ ID NO 1
<211> LENGTH: 444
<212> TYPE: DNA
<213> ORGANISM: Lotus japonicus
<220> FEATURE:
<221> NAME/KEY: CDS
<222> LOCATION: (1)..(444)

<400> SEQUENCE: 1

```
atg ggt ttc act gcg cag caa gag gct cta gtg ggt agc tca tac gaa      48
Met Gly Phe Thr Ala Gln Gln Glu Ala Leu Val Gly Ser Ser Tyr Glu
1               5                   10                  15 aca ttc aag aaa aac ctt cct acc aac agt gtt ttg ttc tac acc gtt      96
Thr Phe Lys Lys Asn Leu Pro Thr Asn Ser Val Leu Phe Tyr Thr Val
            20                  25                  30 ata ttg gag ata gca cca act gca aaa gac atg ttc tcc ttt cta aag     144
Ile Leu Glu Ile Ala Pro Thr Ala Lys Asp Met Phe Ser Phe Leu Lys
        35                  40                  45 gag tct ggg cct aag cat agt cct cag ctc cag gcc cat gct gaa aag     192
Glu Ser Gly Pro Lys His Ser Pro Gln Leu Gln Ala His Ala Glu Lys
    50                  55                  60 gtt ttt gca ctg act cgt gat gct gcc act caa ctc gta gca aaa gga     240
Val Phe Ala Leu Thr Arg Asp Ala Ala Thr Gln Leu Val Ala Lys Gly
65                  70                  75                  80 gaa gtg aca ctt gca gat gcc agc tta ggt gct gtc cac gtt cag aaa     288
Glu Val Thr Leu Ala Asp Ala Ser Leu Gly Ala Val His Val Gln Lys
                85                  90                  95 gcc gtt act gat cct cat ttc gtg gtg gtt aaa gaa gcc ctg ctt caa     336
Ala Val Thr Asp Pro His Phe Val Val Val Lys Glu Ala Leu Leu Gln
            100                 105                 110 aca gta aag gaa gca gtt ggg gcg gac gaa tgg agt gat gac ttg agc     384
Thr Val Lys Glu Ala Val Gly Ala Asp Glu Trp Ser Asp Asp Leu Ser
        115                 120                 125 acc gct tgg gaa gga gca tat gat gga cta gca act gca att aag aag     432
Thr Ala Trp Glu Gly Ala Tyr Asp Gly Leu Ala Thr Ala Ile Lys Lys
    130                 135                 140 gca atg ggt taa                                                     444
Ala Met Gly
145
```

<210> SEQ ID NO 2

<211> LENGTH: 147
<212> TYPE: PRT
<213> ORGANISM: Lotus japonicus

<400> SEQUENCE: 2

```
Met Gly Phe Thr Ala Gln Gln Glu Ala Leu Val Gly Ser Ser Tyr Glu
1               5                   10                  15

Thr Phe Lys Lys Asn Leu Pro Thr Asn Ser Val Leu Phe Tyr Thr Val
            20                  25                  30

Ile Leu Glu Ile Ala Pro Thr Ala Lys Asp Met Phe Ser Phe Leu Lys
        35                  40                  45

Glu Ser Gly Pro Lys His Ser Pro Gln Leu Gln Ala His Ala Glu Lys
    50                  55                  60

Val Phe Ala Leu Thr Arg Asp Ala Ala Thr Gln Leu Val Ala Lys Gly
65                  70                  75                  80

Glu Val Thr Leu Ala Asp Ala Ser Leu Gly Ala Val His Val Gln Lys
                85                  90                  95

Ala Val Thr Asp Pro His Phe Val Val Val Lys Glu Ala Leu Leu Gln
            100                 105                 110

Thr Val Lys Glu Ala Val Gly Ala Asp Glu Trp Ser Asp Asp Leu Ser
        115                 120                 125

Thr Ala Trp Glu Gly Ala Tyr Asp Gly Leu Ala Thr Ala Ile Lys Lys
    130                 135                 140

Ala Met Gly
145
```

<210> SEQ ID NO 3
<211> LENGTH: 483
<212> TYPE: DNA
<213> ORGANISM: Arabidopsis thaliana
<220> FEATURE:
<221> NAME/KEY: CDS
<222> LOCATION: (1)..(483)

<400> SEQUENCE: 3

```
atg gag agt gaa gga aag att gtg ttc aca gaa gag caa gag gct ctt      48
Met Glu Ser Glu Gly Lys Ile Val Phe Thr Glu Glu Gln Glu Ala Leu
1               5                   10                  15 gta gtg aag tct tgg agt gtc atg aag aaa aac tca gct gaa tta ggt      96
Val Val Lys Ser Trp Ser Val Met Lys Lys Asn Ser Ala Glu Leu Gly
            20                  25                  30 ctc aaa ctc ttc atc aag atc ttt gag att gca cca aca acg aag aag     144
Leu Lys Leu Phe Ile Lys Ile Phe Glu Ile Ala Pro Thr Thr Lys Lys
        35                  40                  45 atg ttc tct ttc ttg aga gac tca cca att cct gct gag caa aat cca     192
Met Phe Ser Phe Leu Arg Asp Ser Pro Ile Pro Ala Glu Gln Asn Pro
    50                  55                  60 aag ctc aag cct cac gca atg tct gtt ttt gtc atg tgt tgt gaa tca     240
Lys Leu Lys Pro His Ala Met Ser Val Phe Val Met Cys Cys Glu Ser
65                  70                  75                  80 gca gta caa ctg agg aaa aca ggg aaa gtt acg gtg agg gag act act     288
Ala Val Gln Leu Arg Lys Thr Gly Lys Val Thr Val Arg Glu Thr Thr
                85                  90                  95 ttg aag aga ctt gga gcc agc cat tct aaa tac ggt gtc gtt gac gaa     336
Leu Lys Arg Leu Gly Ala Ser His Ser Lys Tyr Gly Val Val Asp Glu
            100                 105                 110 cac ttt gag gtg gcc aag tat gca ttg ttg gag acg ata aag gag gca     384
His Phe Glu Val Ala Lys Tyr Ala Leu Leu Glu Thr Ile Lys Glu Ala
        115                 120                 125
```

```
gtg ccg gag atg tgg tca ccg gag atg aag gtg gct tgg ggt cag gct    432
Val Pro Glu Met Trp Ser Pro Glu Met Lys Val Ala Trp Gly Gln Ala
    130                 135                 140 tat gat cac ctt gtt gct gcc att aaa gct gaa atg aat ctt tcc aac    480
Tyr Asp His Leu Val Ala Ala Ile Lys Ala Glu Met Asn Leu Ser Asn
145                 150                 155                 160 taa                                                                483

<210> SEQ ID NO 4
<211> LENGTH: 160
<212> TYPE: PRT
<213> ORGANISM: Arabidopsis thaliana

<400> SEQUENCE: 4

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
            35                  40                  45

Met Phe Ser Phe Leu Arg Asp Ser Pro Ile Pro Ala Glu Gln Asn Pro
        50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160

<210> SEQ ID NO 5
<211> LENGTH: 477
<212> TYPE: DNA
<213> ORGANISM: Arabidopsis thaliana
<220> FEATURE:
<221> NAME/KEY: CDS
<222> LOCATION: (1)..(477)

<400> SEQUENCE: 5 atg gga gag att ggg ttt aca gag aag caa gaa gct ttg gtg aag gaa    48
Met Gly Glu Ile Gly Phe Thr Glu Lys Gln Glu Ala Leu Val Lys Glu
1               5                   10                  15 tcg tgg gag ata ctg aaa caa gac atc ccc aaa tac agc ctt cac ttc    96
Ser Trp Glu Ile Leu Lys Gln Asp Ile Pro Lys Tyr Ser Leu His Phe
                20                  25                  30 ttc tca cag ata ctg gag ata gca cca gca gca aaa ggc ttg ttc tct    144
Phe Ser Gln Ile Leu Glu Ile Ala Pro Ala Ala Lys Gly Leu Phe Ser
            35                  40                  45 ttc cta aga gac tca gat gaa gtc cct cac aac aat cct aaa ctc aaa    192
Phe Leu Arg Asp Ser Asp Glu Val Pro His Asn Asn Pro Lys Leu Lys
        50                  55                  60 gct cat gct gtt aaa gtc ttc aag atg aca tgt gaa aca gct ata cag    240
Ala His Ala Val Lys Val Phe Lys Met Thr Cys Glu Thr Ala Ile Gln
65                  70                  75                  80
```

-continued

```
ctg agg gag gaa gga aag gtg gta gtg gct gac aca acc ctc caa tat       288
Leu Arg Glu Glu Gly Lys Val Val Val Ala Asp Thr Thr Leu Gln Tyr
                85                  90                  95 tta ggc tca att cat ctc aaa agc ggc gtt att gac cct cac ttc gag       336
Leu Gly Ser Ile His Leu Lys Ser Gly Val Ile Asp Pro His Phe Glu
            100                 105                 110 gtg gtg aaa gaa gct ttg cta agg aca ttg aaa gag ggg ttg ggg gag       384
Val Val Lys Glu Ala Leu Leu Arg Thr Leu Lys Glu Gly Leu Gly Glu
        115                 120                 125 aaa tac aat gaa gaa gtg gaa ggt gct tgg tct caa gct tat gat cac       432
Lys Tyr Asn Glu Glu Val Glu Gly Ala Trp Ser Gln Ala Tyr Asp His
    130                 135                 140 ttg gct tta gcc atc aag acc gag atg aaa caa gaa gag tca taa           477
Leu Ala Leu Ala Ile Lys Thr Glu Met Lys Gln Glu Glu Ser
145                 150                 155

<210> SEQ ID NO 6
<211> LENGTH: 158
<212> TYPE: PRT
<213> ORGANISM: Arabidopsis thaliana

<400> SEQUENCE: 6

Met Gly Glu Ile Gly Phe Thr Glu Lys Gln Glu Ala Leu Val Lys Glu
1               5                   10                  15

Ser Trp Glu Ile Leu Lys Gln Asp Ile Pro Lys Tyr Ser Leu His Phe
            20                  25                  30

Phe Ser Gln Ile Leu Glu Ile Ala Pro Ala Ala Lys Gly Leu Phe Ser
        35                  40                  45

Phe Leu Arg Asp Ser Asp Glu Val Pro His Asn Asn Pro Lys Leu Lys
    50                  55                  60

Ala His Ala Val Lys Val Phe Lys Met Thr Cys Glu Thr Ala Ile Gln
65                  70                  75                  80

Leu Arg Glu Glu Gly Lys Val Val Val Ala Asp Thr Thr Leu Gln Tyr
                85                  90                  95

Leu Gly Ser Ile His Leu Lys Ser Gly Val Ile Asp Pro His Phe Glu
            100                 105                 110

Val Val Lys Glu Ala Leu Leu Arg Thr Leu Lys Glu Gly Leu Gly Glu
        115                 120                 125

Lys Tyr Asn Glu Glu Val Glu Gly Ala Trp Ser Gln Ala Tyr Asp His
    130                 135                 140

Leu Ala Leu Ala Ile Lys Thr Glu Met Lys Gln Glu Glu Ser
145                 150                 155
```

METHOD FOR ALTERING THE CONTENT OF RESERVE SUBSTANCES IN PLANTS

RELATED APPLICATIONS

This application is a national stage application (under 35 U.S.C. 371) of PCT/EP2003/014774 filed Dec. 23, 2003 which claims benefit to German application 102 60 707.9 filed Dec. 23, 2002.

The invention relates to a method for modifying the storage reserve content of plants by using leghemoglobin- and/or hemoglobin-expressing transformed plants, to corresponding plants, and to their use.

Storage reserves in plants act as reserve materials and are formed by plant tissues and deposited intracellularly. Examples of storage reserves are polysaccharides (carbohydrates such as lichenin, starch, glycogen, polyfructosans), proteins, fats, also polyphosphates and polyhydroxyalkanoates. If required, the storage reserves can be returned to the metabolism and energetics, for example when there is a lack of nutrients, during seed germination, growth and other energy-consuming processes.

Storage reserves are valuable raw materials for nutrition (cereals, nuts, fruit(s), spices and the like) and form the basis for many human foods and can also provide industrial fats and oils. Other storage reserves are used medicinally owing to their pharmacologically active constituents (source: CD Römpp Chemie Lexikon—Version 1.0, Stuttgart/New York: Georg Thieme Verlag 1995).

Also, the storage reserves are increasingly being used as renewable and ecologically acceptable raw materials for industrial purposes, as is possible for example by using starch for the production of packaging materials or, for example, vegetable oils as fuels, such as biodiesel or lubricants.

What are known as secondary metabolites (see also metabolism) of plants (for example pigments, toxins, essential oils, alkaloids, fruit acids) are generally not classified as belonging to the storage reserves (source: Römpp Lexikon Chemie—Version 2.0, Stuttgart/New York: Georg Thieme Verlag 1999 "Reservestoffe" [storage materials]).

In plants, the storage reserves are formed from carbohydrate precursors in seeds or in storage organs. Sucrose is the primary source of carbon and energy, which is transported by the leaves into the developing seeds or into storage organs. The sucrose in the leaves is formed by the starch obtained by photosynthesis. The sucrose which is transported into the developing seeds serves not only for the synthesis of fatty acids for the storage lipids, but also for the synthesis of storage proteins and storage starch.

For example, seeds comprise in total three different forms of storage reserves: storage lipids, storage proteins and starch. Depending on the plants, the ratios between the three storage reserves vary. Thus, for example, oilseed rape varieties comprise approximately 48% storage lipids, 19% starch and 21% storage proteins, while soybean comprises 22% lipids, 12% starch and 37% proteins (Biochemistry & Molecular Biology of the Plant ed. Buchanan, Gruissem, Jones 2000, American Society of Plant Physiologists) based on their dry matter.

The fatty acids which can be obtained from the vegetable oils (lipids) are of particular interest. They are used, for example, as raw materials for plasticizers, lubricants, surfactants, cosmetics and the like, or are employed as valuable raw materials in the food and feedstuff industries. Thus, for example, it is of particular advantage to provide rapeseed oils with medium-chain fatty acids, since these are in particular demand for the production of surfactants.

The targeted modulation of plant metabolic pathways by means of recombinant methods allows the plant metabolism to be advantageously modified in a manner which, if traditional breeding methods were applied, could only be achieved via laborious steps, if at all. Thus, for example, unusual fatty acids, for example certain polyunsaturated fatty acids, are only synthesized in certain plants, or not at all, and can therefore only be produced in a targeted manner by expressing the enzyme in question in transgenic plants (for example Millar et al. (2000) Trends Plant Sci 5:95-101).

As a storage reserve, starch may not only be stored in seeds, but also in other storage organs. Important storage organs for starch are the hypocotyl and roots. Multiplication and enlargement of the cells of the cortical parenchyma give rise to root tubers, such as, for example, potato tubers; swelling of the root collar gives rise to root crops such as, for example, sugar beet or yams.

Thus, for example, starch is the main constituent of the dry matter of potato. In addition to its use as a foodstuff, potatoes are therefore also used as feedstuff and as raw material for obtaining starch and alcohol. In 1988, 269.7 million tonnes of potatoes were harvested globally (source: CD Römpp Chemie Lexikon—Version 1.0, Stuttgart/New York: Georg Thieme Verlag 1995).

The U.S. Pat. No. 6,372,961, WO 98/12913 and WO 00/00597 describe the utilization of hemoglobin or structurally related proteins (myoglobin, bacterial hemoglobin) for increasing the oxygen assimilation in plants. This is intended to improve germination or the energetics of the correspondingly transgenic plants, and to ensure normal growth even under hypoxic conditions. The amount of secondary metabolites which are produced is also said to be increased (WO 98/12913 page 6, line 24). An increased production of storage reserves is not evident from these publications.

It was therefore an object of the present invention to increase the storage reserve content in storage organs of plants to achieve a better utilization of areas under cultivation, fertilizer and the like and to obtain a better yield by means of the plants. In particular, it is intended to improve or make possible the production of starch or oil.

This object is achieved by employing leghemoglobin-expressing transformed plants in the method according to the invention for modifying the storage reserve content in plants. The object is also achieved by leghemoglobin-expressing transformed plants and by their use.

Surprisingly, it has been found that, by expressing a leghemoglobin, storage-reserve-comprising transformed plants are produced which, owing to their (higher) storage reserve content, make possible a better utilization of areas under cultivation, fertilizer and the like and therefore a better yield of storage reserves, in particular starch and oil. An economically advantageous use of the plants according to the invention is therefore possible.

Leghemoglobin belongs to the family of the hemoglobin proteins, whose function is the reversible binding of oxygen and supply. It originates from root nodules of pulses (legumes) and takes the form of a red substance which can be isolated and which is similar to the vertebrates' myoglobin. As a result of the reversible binding of $O_2$, leghemoglobin can ensure the high oxygen demand when nitrogen is fixed by root-nodule bacteria. The apoprotein is formed by the plant cells and the heme by the bacteria (source: CD Römpp Chemie Lexikon—Version 1.0, Stuttgart/New York: Georg Thieme Verlag 1995).

In a further preferred variant of the invention, hemoglobin- or leghemoglobin- and hemoglobin expressing transformed plants are employed in the method according to the invention for modifying the storage reserve content in plants. Accordingly, the present invention also relates to leghemoglobin- and/or hemoglobin-expressing transformed plants and to their use.

In accordance with the invention, hemoglobin is understood as meaning iron(II) complexes of protoporphyrin.

In the present application, expression is understood as meaning the transfer of a genetic information item starting from DNA or RNA into a gene product (polypeptide or protein, in the present case leghemoglobin or hemoglobin), and is also intended to comprise the term overexpression, which means enhanced expression, so that the foreign protein, or the naturally occurring protein, are produced in greater amounts or account for a large part of the total protein content of the host cell.

Transformation is understood as meaning the transfer of genetic information into an organism, in particular a plant. This is meant to include all the ways of introducing the information which are known to the skilled worker, for example microinjection, electroporation, particle bombardment, *agrobacteria*- or chemical-mediated uptake (for example polyethylene-glycol-mediated DNA uptake, or via the silicon carbonate fiber technique). The genetic information can be introduced into the cells for example as DNA, RNA, plasmid or in any other manner and can be incorporated into the host genome by recombination, or else be present in free form or independently as plasmid.

For the purposes of the invention, a transformed plant is thus a genetically modified plant.

Storage reserves are understood as meaning polysaccharides, preferably carbohydrates, proteins, fats, polyphosphates and polyhydroxyalkanoates, especially preferably lichenin, starch, glycogen, polyfructosans.

Among the compounds mentioned, carbohydrates and fats are very especially preferred. Most preferred as storage reserves are starch and oil.

Starch is known to the skilled worker; for further information, reference is made to Römpp Chemie Lexikon—CD Version 2.0, Stuttgart/New York: Georg Thieme Verlag 1999.

For the purposes of the invention, "oil" comprises neutral and/or polar lipids and mixtures of these. Those mentioned in Table 1 are given by way of example, but not by limitation.

TABLE 1

| | Classes of plant lipids |
|---|---|
| Neutral lipids | Triacylglycerol (TAG) |
| | Diacylglycerol (DAG) |
| | Monoacylglycerol (MAG) |
| Polar lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

Neutral lipids preferably mean triacylglycerides. Not only the neutral, but also the polar, lipids may comprise a broad spectrum of different fatty acids. The fatty acids mentioned in Table 2 are given by way of example, but not by limitation.

TABLE 2

Overview over a variety of fatty acids (selection)

| Nomenclature[1] | Name |
|---|---|
| 16:0 | Palmitic acid |
| 16:1 | Palmitoleic acid |
| 16:3 | Roughanic acid |
| 18:0 | Stearic acid |
| 18:1 | Oleic acid |
| 18:2 | Linoleic acid |
| 18:3 | Linolenic acid |
| γ-18:3 | Gamma-linolenic acid* |
| 20:0 | Arachidic acid |
| 22:6 | Docosahexaenoic acid (DHA)* |
| 20:2 | Eicosadienoic acid |
| 20:4 | Arachidonic acid (AA)* |
| 20:5 | Eicosapentaenoic acid (EPA)* |
| 22:1 | Erucic acid |

[1]Chain length: number of double bonds
*do not naturally occur in plants

For further information, reference is likewise made to Römpp Chemie Lexikon—CD Version 2.0, Stuttgart/New York: Georg Thieme Verlag 1999.

In accordance with the invention, all plants are suitable for carrying out the method according to the invention.

"Plant" comprises all annual and perennial monocotyledonous and dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panicum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*.

Preferred are plants from the following plant families: Amaranthaceae, Asteraceae, Brassicacea, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanacea, Sterculiaceae, Tetragoniaceae, Theaceae, Umbelliferae.

Preferred monocotyledonous plants are, in particular, selected from the monocotyledonous crop plants such as, for example, the family Gramineae, such as rice, maize, wheat, or other cereal species such as barley, millet and sorghum, rye, triticale or oats, or sugarcane and all kinds of grasses. The invention is very especially preferably applied to dicotyledonous plant organisms. Preferred dicotyledonous plants are, in particular, selected from the dicotyledonous crop plants, such as, for example, Asteraceae such as sunflower, *tagetes* or *calendula* and others, Compositae, especially the genus *Lactuca*, very particularly the species *sativa* (lettuce) and others, Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and cress or canola and others, Cucurbitaceae such as melon, pumpkin/squash or zucchini and others, Leguminosae, particularly the genus *Glycine*, very particularly the species *max* (soybean), soya, and alfalfa, pea, bean or peanut and others, Rubiaceae, preferably the subclass Lamiidae such as, for example *Coffea arabica* or *Coffea liberica* (coffee bush) and others, Solanaceae, particularly the genus *Lycopersicon*, very particularly the species *esculentum* (tomato), the genus *Solanum*, very particularly the species *tuberosum* (potato) and *melongena* (aubergine) and tobacco or paprika and others, Sterculiaceae, preferably the subclass Dilleniidae such as, for example, *Theobroma cacao* (*cacao* bush) and others, Theaceae, preferably the subclass Dilleniidae such as, for example, *Camellia sinensis* or *Thea sinensis* (tea bush) and others, Umbelliferae, particularly the genus *Daucus* (very particularly the species *carota* (carrot)) and *Apium* (very particularly the species *graveolens dulce* (celery)) and others; and the genus *Capsicum*, very particularly the genus *annum* (pepper) and others, and linseed, soya, cotton, hemp, flax, cucumber, spinach, carrot, sugar beet and the various tree, nut and grapevine species, in particular banana and kiwi fruit.

Also encompassed are ornamental plants, useful or ornamental trees, flowers, cut flowers, shrubs or turf. Plants which may be mentioned by way of example but not by limitation are angiosperms, bryophytes such as, for example, Hepaticae (liverworts) and Musci (mosses); pteridophytes such as ferns, horsetail and clubmosses; gymnosperms such as conifers, cycads, ginkgo and Gnetalae, the families of the Rosaceae such as rose, Ericaceae such as rhododendron and azalea, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums Liliaceae such as dracena, Moraceae such as ficus, Araceae such as philodendron and many others.

Furthermore, plant organisms for the purposes of the invention are further organisms capable of being photosynthetically active such as, for example, algae, cyanobacteria and mosses. Preferred algae are green algae such as, for example, algae from the genus *Haematococcus, Phaedactylum tricornatum, Volvox* or *Dunaliella*. *Synechocystis* is particularly preferred.

Most preferred are oil plants, i.e. plants which already naturally have a high oil content and/or which are used for the industrial production of oils. These plants may have a high oil content and/or a particular fatty acid composition which is of industrial interest. Preferred plants have a lipid content of at least 1%. Oil plants comprise for example: *Borago officinalis* (borage); *Brassica* species such as *B. campestris, B. napus, B. rapa* (mustard or oilseed rape); *Cannabis sativa* (hemp); *Carthamus tinctorius* (safflower); *Cocos nucifera* (coconut); *Crambe abyssinica* (crambe); *Cuphea* species (*Cuphea* species provide medium-chain fatty acids, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Helianthus annuus* (sunflower); *Linum usitatissimum* (linseed or flax); *Oenothera biennis* (evening primrose); *Olea europea* (olive); *Oryza sativa* (rice); *Ricinus communis* (castor-oil plant); *Sesamum indicum* (sesame); *Glycine max* (soybean); *Triticum* species (wheat); *Zea mays* (maize), and various nut species such as, for example, walnut or almond.

If the plants used belong to the plants of the genus *Leguminosae* (pulses), the scope of the invention encompasses the expression of foreign proteins (leghemoglobins, hemoglobin), i.e. hemoglobins and/or leghemoglobins which do not occur naturally as symbionts or the modification of the plants in such a way that they overexpress the naturally occurring leghemoglobin.

Most preferred are potatoes, *Arabidopsis thaliana* and oilseed rape.

It is advantageous for the abovementioned plants to express a leghemoglobin and/or hemoglobin selected from the group consisting of leghemoglobin and/or hemoglobin from the plants *Lupinus luteus* (LGB1_LUPLU, LGB2_LUPLU), *Glycine max* (LGBA_SOYBN, LGB2_SOYBN, LGB3_SOYBN), *Medicago sativa* (LGB1-4_MEDSA), *Medicago trunculata* (LGB1_MEDTR), *Phaseolus vulgaris* (LGB1_PHAVU, LGB2_PHAVU), *Vicia faba* (LGB1_VICFA, LGB2_VICFA), *Pisum sativum* (LGB1_PEA, LGB2_PEA), *Vigna unguiculata* (LGB1_VIGUN), *Lotus japonicus* (LGB_LOTJA), *Psophocarpus tetragonolobus* (LGB_PSOTE), *Sesbania rostrata* (LGB1_SESRO), *Casuarina glauca* (HBPA_CASGL) and *Canvalaria lineata* (HBP_CANLI) *Physcomitrella patens* (HBL0_PHYPA), *Arabidopsis thaliana* (HBL1_ARATH, HBL2_ARATH), *Gossypium hirsutum* (HBL1_GOSHI, HBL2_GOSHI), *Medicago sativa* (HBL1_MEDSA), *Oryza sativa* (HBL1_ORYSA, HBL2_ORYSA, HBL3_ORYSA, HBL4_ORYSA), *Brassica napus* (HBL2_BRANA), *Lycopersicon esculentum* (HBL2_LYCES), *Hordeum vulgare* (HBL_HORVU), *Zea mays* (HBL_MAIZE), *Trema tomentosa* (HBL_TRETO), *Casuarina glauca* (HBP1_CASGL, HBP2_CASGL, HBPA_CASGL), *Parasponia rigida* (HBPL_PARAD). The Swiss-Prot database entries are shown in each case in brackets.

Especially advantageous plants are those which comprise the sequence of SEQ ID NO: 1 coding for leghemoglobin and/or the sequences of SEQ ID NOS: 3 and/or 5 coding for hemoglobin. Leghemoglobin and/or hemoglobin from *Lotus japonicus* is preferably employed. The transformed plants will now produce an increased amount of storage reserves.

The invention also encompasses plants which, in order to produce storage reserves, express a leghemoglobin as shown in sequence of SEQ ID NO: 1 and/or a hemoglobin as shown in sequences of SEQ ID NOS: 3 and 5.

A preferred variant of the invention takes the form of plants which express the leghemoglobin and/or hemoglobin in a storage-organ-specific manner.

As a rule, the abovementioned plants deposit the storage reserves in specific organs. Examples are bulbs, tubers, seeds, kernels, nuts, leaves and the like. For the purposes of the invention, storage organs are also understood as meaning fruits. Fruits are the collective term for the organs of the plants which surround the seed as nutritive tissue. Mention should be made not only of the edible fruits, in particular "fruit", but also of pulses, cereals, nuts, spices, and also of apothecary drugs (cf. fructus, semen). Naturally, storage of the storage reserves may also take place in all of the plant.

The leghemoglobin and/or hemoglobin is preferably expressed in a tuber-specific or seed-specific manner.

Plants which are suitable are all those mentioned above. The following are preferred: potatoes, *Arabidopsis thaliana*, oilseed rape, soybeans, peanuts, maize, cassava, yams, rice, sunflowers, rye, barley, hops, oats, durum wheat and aestivum wheat, lupins, peas, clover, beet, cabbage, vines and the like as they can be found in the directive on the cultivar list of the Saatgutverkehrsgesetz [German seed trading act] (Blatt für PMZ [official gazette for patents and trademark law] 1986, p. 3, last modified in Blatt für PMZ 2002, p. 68).

Especially preferred are tuber-producing plants, in particular potato plants, or seed-producing plants, in particular *Arabidopsis thaliana*, oilseed rape or soybean.

The tissue-specific expression can be achieved for example by using a tissue-specific promoter. Such a tissue-specific expression is known for example from U.S. Pat. No. 6,372,961 B1 column 11, lines 44 et seq.

The invention furthermore relates to a nucleotide sequence as shown in sequence of SEQ ID NO: 1 coding for leghemoglobin for use in a plant and a corresponding gene structure or vector and their use for transforming a plant with the invention.

In particular, the invention also encompasses the use of a leghemoglobin-encoding nucleotide sequence which has approximately 70%, preferably 80%, especially preferably 85%, 90%, in particular 91%, 92%, 93%, 94%, 95%, 96%, 97%, 98% or 99% identity with the sequence of SEQ ID NO: 1.

The invention furthermore relates to nucleotide sequences as shown in SEQ ID NOS: 3 and 5 coding for hemoglobin for use in a plant and a corresponding gene structure or vector and their use for transforming a plant. In particular, the invention also encompasses the use of hemoglobin-encoding nucleotide sequences which have approximately 70%, preferably 80%, especially preferably 85%, 90%, in particular 91%, 92%, 93%, 94%, 95%, 96%, 97%, 98% or 99% identity with the sequences of SEQ ID NOS: 3 and 5.

The term nucleotide sequence is understood as meaning all nucleotide sequences which (i) correspond exactly to the sequences shown; or (ii) comprise at least one nucleotide sequence which, within the limits of the degeneracy of the genetic code, corresponds to the sequences shown; or (iii) comprises at least one nucleotide sequence which hybridizes with a nucleotide sequence which is complementary to the nucleotide sequence (i) or (ii), and, if appropriate, (iiii) comprises function-neutral sense mutations in (i). In this context, the term "function-neutral sense mutations" means the substitution of chemically similar amino acids such as, for example, glycine by alanine or serine by threonine.

Also encompassed in accordance with the invention are the sequence regions which precede (5', or upstream) and/or follow (3', or downstream) the coding regions (structural genes). In particular, this includes sequence regions with a regulatory function. They can affect transcription, RNA stability, RNA processing and translation. Examples of regulatory sequences are, inter alia, promoters, enhances, operators, terminators or translation enhancers.

The proteins in question (leghemoglobins and/or hemoglobins) also include isoforms, which are understood as meaning proteins with the same or a comparable action but a different primary structure.

In accordance with the invention, modified forms are understood as meaning proteins which comprise modifications in the sequence, for example at the N- and/or C-terminus of the polypeptide or in the region of conserved amino acids, without, however, adversely affecting the function of the protein. These modifications can be carried out by known methods in the form of amino acid substitutions.

The invention is described in detail with reference to the following experiments.

EXAMPLES

1. Model Organisms

Potato and *Arabidopsis thaliana* were employed as model organisms for the experiments. The two plant species represent a member of the Higher Plants (spermatophytes). Owing to the high degree of homology of their DNA sequences or polypeptide sequences, they can be employed as model plants for other plant species.

2. General Methods a) Culture of Potato or *Arabidopsis* Plants

*Arabidopsis* plants were grown either on Murashige-Skoog medium supplemented with 0.5% sucrose (Ogas et al., 1997 Science 277:91-94) or on compost (Focks & Benning, 1998 Plant Physiology 118:91-101). To obtain uniform germination and flowering times, the seeds were first plated, or scattered on compost, and then stratified for two days at 4° C. After flowering, the pods were labeled. Then, in accordance with the labels, pods were harvested post-flowering at an age of 6-20 days. Potato plants were grown as described by Dietze et al., 1995 (Gene Transfer to Plants, Eds. Potrykus and Spangenberg, Springer Lab Manual, Berlin, Heidelberg, 24-29).

b) Isolation of Total RNA and poly-A+ RNA from Plants

RNA and polyA+ RNA are isolated in order to generate expression constructs. RNA was isolated from *Arabidopis* pods or potato tubers or roots of *Lotus japonicus* as described in the protocol which follows:

plant material aged 6-40 days was harvested and shock-frozen in liquid nitrogen. Until further use, the material was stored at −80° C. 75 mg of the material were ground to a fine powder in the cooled mortar and treated with 200 μl of the lysis buffer of the Ambion RNAqueos kit. Then, total RNA was isolated following the manufacturer's instructions. The RNA was eluted with 50 μl of elution buffer (Ambion), and the concentration was determined using a photometer (Eppendorf) at 260 nm on the basis of the absorption of a 1:100 dilute solution. 40 μg/ml RNA corresponds to an absorption of 1. The RNA solutions were brought to a concentration of 1 μg/μl using RNAse-free water. The concentrations were checked by agarose gel electrophoresis.

To isolate polyA+ RNA, oligo(dT) cellulose from Amersham Pharmacia was used following the manufacturer's instructions. RNA and polyA+ RNA were stored at −70° C.

3. Construction of the cDNA Library

To construct the cDNA library from *Lotus japonicus* and *Arabidopsis thaliana* RNA, the first-strand synthesis was achieved using reverse transcriptase from mouse leukemia virus (Clontech) and Oligo-d(T) primers, while the second-strand synthesis was achieved by incubation with DNA polymerase I, Klenow enzyme and RNAse H cleavage at 12° C. (2 hours), 16° C. (1 hour) and 22° C. (1 hour). The reaction was quenched by incubation at 65° C. (10 minutes) and subsequently transferred onto ice. Double-stranded DNA molecules were made blunt-ended at 37° C. (30 minutes) using T4 DNA polymerase (Roche, Mannheim). The nucleotides were removed by phenol/chloroform extraction and Sephadex G50 centrifuge columns. EcoRI/NotI adapters (Pharmacia, Freiburg, Germany) were ligated onto the cDNA ends by means of T4 DNA ligase (Roche, 12° C. overnight), re-cut with NotI and phosphorylated by incubation with polynucleotide kinase (Roche, 37° C., 30 minutes). This mixture was subjected to separation on a low-melting agarose gel. DNA molecules over 200 base pairs were eluted from the gel, phenol-extracted, concentrated on Elutip D columns (Schleicher und Schüll, Dassel, Germany) and ligated into the cloning vector pSPORT1 (Invitrogen, Karlsruhe), using the manufacturer's material and following their instructions.

4. DNA Sequencing and Computer Analysis cDNA libraries as described in section 2 were used for DNA sequencing by standard methods, in particular by the chain termination method using the ABI PRISM Big Dye Terminator Cycle Sequencing Ready Reaction kit (Perkin-Elmer, Weiterstadt, Germany). The sequencing of random single clones was carried out after the preparative plasmid preparation from cDNA libraries via in-vivo bulk excision and retransformation of DH5α on agar plates (details on materials and protocol from Stratagene, Amsterdam, the Netherlands). Plasmid DNA was prepared from *E. coli* overnight cultures which had been grown in Luria broth supplemented with ampicillin (see Sambrook et al. (1989) (Cold Spring Harbor Laboratory Press: ISBN 0-87969-309-6)) on a Qiagen DNA preparation robot (Qiagen, Hilden) following the manufacturer's protocols.

The sequences were processed and annotated using the standard software package EST-MAX, which is commercially available from Bio-Max (Munich, Germany). Using comparative algorithms and a query sequence, a search for homologous genes was performed with the aid of the BLAST program (Altschul et al. (1997) "Gapped BLAST and PSI-BLAST: a new generation of protein database search programs", Nucleic Acids Res. 25:3389-3402).

5. Generation of the Expression Constructs for the Tuber-Specific Expression in Potato, and the Seed-Specific Expression in *Arabidopsis* a) Tuber-Specific Expression

The leghemoglobin gene Lljlb was excised from the vector pSportI using NotI and KpnI, the NotI cleavage site being made blunt-ended by incubation with Klenow enzyme. For ligation into the vector pART33, the latter was digested with BamHI, the cleavage site was then made blunt-ended by incubation with Klenow enzyme and the product was subsequently digested with KpnI. pART33 already comprises the B33 promoter (1459 bp; Liu X J, Prat S, Willmitzer L, Frommer W B (1990) cis regulatory elements directing tuber-specific and sucrose-inducible expression of a chimeric class I patatin promoter/GUS-gene fusion. Mol Gen Genet. 223(3): 401-6) and the OCS terminator (766 bp) for tuber-specific expression. The total construct was excised from pART33 using NotI and cloned into the plant transformation vector pART27.

b) Seed-Specific Expression

The leghemoglobin gene Lljlb was recloned from the vector pART33 into the vector pBINUSP. To this end, the construct pART33-LegHb was first digested with Asp718I and the overhangs were made blunt-ended with Klenow fragment. Thereafter, the linearized construct was digested with XbaI and the gene thus obtained was ligated overnight at 4° C. into the XbaI/SmaI-cut pBINUSP.

The hemoglobin gene 1 AtHb1 was recloned from the vector pART33 into the vector pBINUSP. To this end, the construct pART33-AtHb1 was first digested with Asp718I and the overhangs were made blunt-ended with Klenow fragment. Thereafter, the linearized construct was digested with XbaI and the gene thus obtained was ligated overnight at 4° C. into the XbaI/SmaI-cut pBINUSP.

The hemoglobin gene 2 AtHb2 was recloned from the vector pART33 into the vector pBINUSP. To this end, the construct pART33-AtHb2 was first digested with Asp718I and the overhangs were made blunt-ended with Klenow fragment. Thereafter, the linearized construct was digested with XbaI and the gene thus obtained was ligated overnight at 4° C. into the XbaI/SmaI-cut pBINUSP.

6. Plant Transformation Plasmids

Binary vectors such as pBIN can be used for transforming plants (Bevan, M., Nucleic Acids Res. 12 (1984), 8711-8721). The binary vectors can be constructed by ligating the cDNA in sense or antisense orientation into T-DNA. 5' of the cDNA, a plant promoter activates the transcription of the cDNA. A polyadenylation sequence is located 3' of the cDNA.

Tissue-specific expression can be achieved using a tissue-specific promoter. For example, seed-specific expression can be achieved by cloning the napin or the LeB4 or the USP promoter 5' of the cDNA. Any other seed-specific promoter element may also be used. The CaMV 35S promoter may be used for achieving constitutive expression in the whole plant.

7. Transformation of *agrobacterium*, and Plant Transformation

The *agrobacterium*-mediated transformation of plants can be carried out for example using the *Agrobacterium tumefaciens* strain GV3101 (pMP90) (Koncz and Schell, Mol. Gen. Genet. 204 (1986) 383-396) or LBA4404 (Clontech). The bacterium can be transformed using standard transformation techniques with which the skilled worker is familiar (Deblaere et al., Nucl. Acids. Tes. 13 (1984), 4777-4788).

The *agrobacterium*-mediated transformation of plants itself can likewise be carried out by standard transformation and regeneration techniques known to the skilled worker (Gelvin, Stanton B., Schilperoort, Robert A., Plant Molecular Biology Manual, 2nd Ed., Dordrecht: Kluwer Academic Publ., 1995, in Sect., Ringbuch Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 S., ISBN 0-8493-5164-2).

The transformation of *Arabidopsis thaliana* by means of *Agrobacterium* was carried out by the method of Bechthold et al., 1993 (C.R. Acad. Sci. Ser. III Sci. Vie., 316, 1194-1199). The method was modified in as far as the vacuum infiltration was dispensed with.

For the transformation, *Arabidopsis thaliana* Col0 seeds were sown on moistened compost, stratified for two days at 4° C. and grown for 4-6 weeks under short-day conditions (8 hours light, 21° C.). To induce flowering, the plants were then transferred to long half day conditions (16 hours light, 21° C.). After approximately 10 days, the inflorescence is large enough for immersion. The inflorescence is immersed in an *Agrobacterium* suspension in ½ MS solution (Murashige and Skoog, see hereinbelow) pH 5.7, 5% sucrose, 44 µM benzylaminopurin (Sigma) and 0.03% Silwet L-77 (Lehle Seeds, USA). The optical density of the *Agrobacterium* suspension at 600 nm should be 0.8. The bacteria are previously grown in YEB medium (0.5% Bactotrypton, 0.5% Bactopeptone, 0.1% yeast extract, 0.5% sucrose and 2 mM $MgCl_2$).

After immersion of the plants, moistening of the latter continued for approximately three more weeks. Then, irrigation was stopped, and the plants desiccated to obtain seeds. The seeds obtained were plated on plates with ½ MS solution, pH 5.7, 50 µg kanamycin, 250 µg Timenten and 0.8% agar. Resistant seedlings were pricked out individually into compost.

The transformation of potato (*Solanum tuberosum* L.) was carried out by the method of Dietze et al. in Gene transfer to plants (Eds. I. Potrykus and G. Spangenberg, Springer Lab Manual, 1995, pp. 24-29). The starting material used was the cultivar Desiree.

For the transformation, five to six leaves of a sterile shoot culture of potato variety Desiree were equilibrated carefully in 10 ml of a 2 MS solution (standard MS medium of Murashige and Skoog (1962) A revised medium for rapid growth and bioassays with tobacco tissue cultures. Physiol. Plant., 15, 473-497.) supplemented with 2% of sucrose. Sections 1-2 mm in length are excised from the leaves transverse to the central vein and placed into fresh 2 MS medium. 50 µl of a solution of *agrobacteria* which have been transformed with the T plasmid pART27-JpLeg are added to the fresh medium. The agrobacterial solution is distributed over the leaf segments, and the plates are incubated for two days in the dark at 22-24° C. After two days, the leaf segments are transferred to CIM medium (MS medium supplemented with 1.5% glucose, 5 mg/l NAA, 0.1 mg/l BAP, 250 mg/l Claforin and 50 mg/l kanamycin or hygromycin) and incubated for 7 days. The leaf segments are then transferred to SIM medium (MS medium supplemented with 2 mg/l zeatin, 0.02 mg/l NAA, 0.02 mg/l GA3, 250 mg/l Claforin and 50 mg/l kanamycin or hygromycin). After 1-2 weeks, the resulting transgenic shoots (1-1.5 cm in length) can then be excised and transferred to RIM medium (MS medium supplemented with 250 mg/l Claforin). After 3-4 weeks, the shoots have formed leaves and roots, and the plants can be pricked out into compost.

In accordance with this method, 2-3 independent transgenic lines can be obtained for each leaf employed.

The plant transformation using particle bombardment, polyethylene-glycol-mediated DNA uptake or via the silicon carbonate fiber technique, which is another alternative, is described, for example, by Freeling and Walbot "The maize handbook" (1993) ISBN 3-540-97826-7, Springer Verlag New York).

8. Analysis of the Leghemoglobin and Hemoglobin Expression in the Transformed Plant The leghemoglobin activity in the transformed plant was measured at the transcription level.

A suitable method for determining the transcription level of the gene (which indicates the amount of RNA which is available for the translation of the gene) is to carry out a Northern blot as described hereinbelow (for reference, see Ausubel et al. (1988) Current Protocols in Molecular Biology, Wiley: New York, or the abovementioned Examples section), where a primer which is such that it binds to the leghemoglobin is labeled with a detectable label (usually a radiolabel or chemiluminescence label) so that, when the total RNA of a culture of the organism is extracted, separated on a gel, transferred to a stable matrix and incubated with this probe, the binding and extent of the binding of the probe indicates the presence and also the amount of the mRNA for the gene in question (leghemoglobin or hemoglobin). This information indicates the degree of transcription of the transformed gene. Cellular total RNA can be prepared from cells, tissues or organs using a plurality of methods, all of which are known in the art, such as, for example, the method described by Bormann, E. R., et al. (1992) Mol. Microbiol. 6:317-326.

Northern Hybridization:

For the RNA hybridization, 20 µg of total RNA or 1 µg of poly(A)$^+$ RNA were separated by means of gel electrophoresis in agarose gels with a strength of 1.25% using formaldehyde, as described in Amasino (1986, Anal. Biochem. 152, 304), transferred to positively charged nylon membranes (Hybond N+, Amersham, Braunschweig) by capillary attraction using 10×SSC, immobilized by means of UV light and prehybridized for 3 hours at 68° C. using hybridization buffer (10% (w/v) dextran sulfate, 1 M NaCl, 1% SDS, 100 mg herring sperm DNA). Labeling of the DNA probe with the Highprime DNA Labeling kit (Roche, Mannheim, Germany) was carried out during the prehybridization step using alpha-$^{32}$P-dCTP (Amersham Pharmacia, Braunschweig, Germany). The hybridization was performed in the same buffer overnight at 68° C. after the labeled DNA probe had been added. The wash steps were carried out twice for 15 minutes using 2×SSC and twice for 30 minutes using 1×SSC, 1% SDS, at 68° C. Exposure of the sealed filters was carried out at −70° C. for a period of 1 to 14 days.

9. Analysis of the Effect of the Recombinant Leghemoglobin on the Production of the Desired Product The effect of the genetic modification in plants, fungi, algae, ciliates, or on the production of a desired compound (such as a fatty acid) can be determined by growing the modified microorganisms or the modified plant under suitable conditions (such as those described hereinabove) and analyzing the medium and/or the cellular components for the increased production of the desired product (i.e. of lipids or carbohydrates). These analytical techniques are known to the skilled worker and comprise spectroscopy, thin-layer chromatography, various types of staining methods, enzymatic and microbiological methods, and analytical chromatography such as high-performance liquid chromatography (see, for example, Ullman, Encyclopedia of Industrial Chemistry, Vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1);

"Progress in Lipid Research, Oxford: Pergamon Press, 1 (1952)-16 (1977) under the title: Progress in the Chemistry of Fats and Other Lipids CODEN.

To determine the overall efficiency with which the compound is produced, it is also possible, in addition to measuring the fermentation end product, to analyze other components of the metabolic pathways which are used for producing the desired compound, such as intermediates and secondary products. The analytical methods comprise measurements of the nutrient quantities in the medium (for example sugars, hydrocarbons, nitrogen sources, phosphate and other ions), measurements of the biomass composition and of the growth, analysis of the production of usual metabolites via biosynthetic pathways, and measurements of gases which are generated during the fermentation process. Standard methods for these measurements are described in Applied Microbial Physiology; A Practical Approach, P. M. Rhodes and P. F. Stanbury, Ed., IRL Press, pp. 103-129; 131-163 and 165-192 (ISBN: 0199635773) and references cited therein.

One example is the analysis of fatty acids (abbreviations: FAMEs, fatty acid methyl esters; GC-MS, gas liquid chromatography/mass spectrometry; TAG, triacylglycerol; TLC, thin-layer chromatography).

Unequivocal proof for the presence of fatty acid products can be obtained by analyzing recombinant organisms following standard analytical procedures: GC, GC-MS or TLC, as variously described by Christie and references therein (1997, in: Advances on Lipid Methodology, Fourth edition: Christie, Oily Press, Dundee, 119-169; 1998, Gaschromatographie-Massenspektrometrie-Verfahren [Gas-chromatographic/mass-spectrometric method], Lipide 33:343-353).

The material to be analyzed can be disrupted by sonication, grinding in a glass mill, liquid nitrogen and milling, or via any other applicable method. After disruption, the material has to be centrifuged. The sediment is resuspended in distilled water, heated for 10 minutes at 100° C., cooled on ice and recentrifuged, followed by extraction for 1 hour at 90° C. in 0.5 M sulfuric acid in methanol with 2% dimethoxypropane, which results in hydrolyzed oil and lipid compounds, which give transmethylated lipids. These fatty acid methyl esters are extracted in petroleum ether and finally subjected to GC analysis using a capillary column (Chrompack, WCOT Fused Silica, CP-Wax-52 CB, 25 micrometers, 0.32 mm) at a temperature gradient for 20 minutes at between 170° C. and 240° C. and 5 minutes at 240° C. The identity of the resulting fatty acid methyl esters must be defined using standards which are available from commercial sources (i.e. Sigma).

10. Analysis of the Expression of Lotus Leghemoglobin, Arabidopsis Hemoglobin 1, Arabidopsis Hemoglobin 2 in Maturing Seeds of Arabidopsis To verify the expression of the transgenes hemoglobin 1 and hemoglobin 2 from *Arabidopsis thaliana* (AtHb1 and AtHb2) and, respectively leghemoglobin from *Lotus japonicus* (LjLegHb), Northern blot analyses were carried out. To this end, total RNA from maturing seeds of transgenic plants and wild-type plants was isolated and separated by electrophoresis, and transcripts were detected using the corresponding digoxigenin-labeled probes. 2-4 independent analyses were carried out for each line. By way of example, FIG. 1 shows the results of the expression analyses with maturing T2 seeds of transgenic *Arabidopsis* lines which express either *Lotus* hemoglobin (LjLegHb), *Arabidopsis* hemoglobin 1 (AtHb1) or *Arabidopsis* hemoglobin 2 (AtHb2). The transformed gene is transcribed in almost all of the analyzed lines since the corresponding mRNA can be detected. In the controls, in contrast, no transcript can be detected.

11. Analysis of the Oil Content of Transformed Arabidopsis Plants which Express Lotus Leghemoglobin and Arabidopsis Hemoglobins The oil content in the seeds of transgenic *Arabidopsis* plants which express *Lotus* leghemoglobin, *Arabidopsis* hemoglobin 1 or *Arabidopsis* hemoglobin 2 are determined indirectly via the quantification of the total fatty acids. The following protocol is used for this purpose:

The lipids were extracted from the seeds by the method of Blight & Dyer, 1959 Can. J. Biochem. Physiol. 37:911. For each measurement, 5-10 seeds are transferred into 1.2 ml Qiagen microtubes (Qiagen, Hilden), pulverized in a Retsch mill (MM300, Retsch (Haan)), and the total lipids are extracted by addition of 500 µl of chloroform/methanol (2:1, contains pentadecanoic acid (C15) as internal standard). After addition of 500 µl of 50 mM potassium phosphate buffer pH 7.5, the phases are separated. The organic phase is transferred into a Pyrex tube and evaporated to dryness. This is followed by the derivatization of the total fatty acids to give fatty acid methyl esters, using the method of Benning & Sommerville, 1992 J. Bacteriol. 174: 6479-6487 by addition of 1 N $H_2SO_4$ in methanol and 2% (v/v) dimethoxypropanes for 1 hour at 80° C. These fatty acid methyl esters are extracted in petroleum ether and finally analyzed by gas chromatography using a capillary column (Chrompack, WCOT Fused Silica, CP-Wax-52, 25 micrometers 0.32 mm). The total fatty acids are quantified by comparing the signal areas of the fatty acid methyl esters with the signal area of the internal standard of known concentration. A further indicator for the oil content in *Arabidopsis thaliana* is the amount of the fatty acid Eicosenoic acid ($20:1^{\Delta 11}$), which is found virtually exclusively in the storage lipids.

After the transformation of *Arabidopsis thaliana*, transgenic lines are selected via resistance to antibiotics. To this end, T1 seeds of transformed *Arabidopsis* plants were germinated on hygromycin-containing selection plates. For the quantitative determination of the oil contents, T2 seeds of in each case 4 independent transgenic lines were analyzed. 5-9 independent measurements were carried out for the individual lines, and the corresponding means were calculated.

The results of the determination of the oil contents in mature T2 seeds of transgenic plants which express *Lotus* leghemoglobin are shown by way of example in Table 3 and in FIG. 2. In accordance with the invention, the expression of the *Lotus* leghemoglobin in lines 4 and 5 results in a significant increase in the oil content by 17.14% and 17.54%, respectively.

The results of the determination of the oil contents in mature T2 seeds of transgenic plants which express *Arabidopsis* hemoglobin 1 are shown by way of example in Table 4 and in FIG. 3. In accordance with the invention, the expression of *Arabidopsis* hemoglobin 1 in lines 35, 13 and 39 leads to a significant increase in the oil content by 9.78%, 12.22% and 51.16%, respectively.

The results of the determination of the oil contents in mature T2 seeds of transgenic plants which express *Arabidopsis* hemoglobin 2 are shown by way of example in Table 5 and in FIG. 4. In accordance with the invention, the expression of *Arabidopsis* hemoglobin 2 in lines 2, 10 and 11 leads to a significant increase in the oil content by 16.25%, 21.86% and 23.80%, respectively.

12. Determination of the Starch Content in Transformed Potato Plants which Express *Lotus* Leghemoglobin The density measurement as described by Schéele C. von, Svensson, G. and Rasmusson J., Die Bestimmung des Stärkegehalts und der Trockensubstanz der Kartoffel mit Hilfe des spezifischen Gewichts [Determination of the starch content and the dry matter of potatoes with the aid of the specific gravity]. Landw. Vers Sta. 127: 67-96, 1937 is employed for determining the starch content and tubers of the potato plants. The density measurement can then be converted and the result used for estimating the starch content. The following formula was employed for the conversion:

The specific density was determined by weighing the tubers both in the air and in water, with x being the mass in air and y the mass in water. The specific density is then the result of x/(x−y). Furthermore, the mean of 560 measured samples was calculated and the following relationships established (Burton W. G. (1989) The Potato. Longman, New York):

% dry matter=24.182+[211.04*(sp. density−1.0988)]

% starch=17.546+[199.07*(sp. density−1.0988)]

Differently sized potato tubers from a variety of transgenic lines and of the control plants were employed for measuring the leghemoglobin-expressing plants and, for comparison purposes, the control plants. The different sizes serve for reproducing the observed effect in all tuber sizes.

Work-up or the recovery of starch from the leghemoglobin-expressing potatoes can be carried out by the customary methods with which the skilled worker is familiar, for example as detailed in U.S. patent application 2001/0041199 A1, page 4, example 1.

To measure the starch content in the tubers of the leghemoglobin-expressing plants and, for comparison purposes, of the control plants, the plants were grown both in the greenhouse and in the polyhouse. The different cultivation methods serve for reproducing the observed effect under different climatic conditions. Differently sized potato tubers were employed for the measurements in order to reproduce the observed effect in all tuber sizes.

By way of example, Table 6 shows the data of a transgenic line in comparison with control plants, all of which have been grown in the greenhouse. In each case 6 measurements of different tubers from one line and the resulting means and standard deviations are shown. In accordance with the invention, a significant increase in the starch content by 40.77% was detected in the transgenic line. Similar values were obtained with further lines.

FIG. 5 shows the average starch contents of four independent transgenic lines in comparison with the control plants, all of which had been grown in the period from May 2003 to September 2003 in the polyhouse in Golm. The average data are based on 334 tubers (line 13), 358 tubers (line 57), 380 tubers (line 45), 384 tubers (line 54) and 151 tubers (wild type). In accordance with the invention, a significant increase in the starch content in the tubers of the leghemoglobin-expressing transformed plants was also observed under the climatic conditions which prevailed in the polyhouse, which confirmed the results obtained from the greenhouse. The temperature conditions which prevailed in the polyhouse during the culturing period are shown in FIG. 6.

TABLE 3

Oil contents in T2 seeds of transgenic *Arabidopsis* lines which express LjLegHb in comparison with the control. The individual measurements were carried out on in each case 5-10 seeds, and the corresponding oil contents are shown as µg fatty acids per seed.

| Line | WT | Line 1.1.9 | Line 3 | Line 5 | Line 4 |
|---|---|---|---|---|---|
|  | 6.39 | 9.86 | 6.46 | 8.43 | 8.64 |
|  | 9.38 | 9.79 | 6.87 | 9.04 | 8.99 |
|  | 9.38 | 8.98 | 7.89 | 8.91 | 9.18 |
|  | 7.48 | 9.72 | 9.45 | 8.77 | 8.43 |
|  | 9.38 | 7.78 | 8.16 |  | 6.57 |
|  | 6.87 | 7.54 | 8.30 |  | 10.74 |
|  | 8.44 | 7.59 | 6.97 |  |  |
|  | 6.03 | 4.31 |  |  |  |
|  | 3.93 |  |  |  |  |
| Mean | 7.48 | 8.20 | 7.73 | 8.79 | 8.76 |
| Standard deviation | 1.77 | 1.74 | 0.96 | 0.23 | 1.23 |
| Relative oil gain |  | 9.61 | 3.34 | 17.54 | 17.14 |

TABLE 4

Oil contents in T2 seeds of transgenic *Arabidopsis* lines which express AtHb1 in comparison with the control. The individual measurements were carried out on in each case 5-10 seeds, and the corresponding oil contents are shown as µg fatty acids per seed.

| Line | WT | Line 39 | Line 35 | Line 17 | Line 13 |
|---|---|---|---|---|---|
|  | 6.39 | 12.17 | 8.13 | 7.96 | 8.02 |
|  | 9.38 | 11.02 | 7.48 | 6.73 | 9.04 |
|  | 9.38 | 10.54 | 7.82 | 7.45 | 8.16 |
|  | 7.48 | 10.13 | 7.89 | 6.05 | 8.09 |
|  | 9.38 | 9.93 | 9.72 |  | 8.64 |
|  | 6.87 | 13.40 |  |  |  |
|  | 8.44 | 11.36 |  |  |  |
|  | 6.03 | 11.22 |  |  |  |
|  | 3.93 | 11.97 |  |  |  |
| Mean | 7.48 | 11.30 | 8.21 | 7.05 | 8.39 |
| Standard deviation | 1.77 | 1.03 | 0.79 | 0.72 | 0.39 |
| Relative oil gain |  | 51.16 | 9.78 | −5.77 | 12.22 |

TABLE 5

Oil contents in T2 seeds of transgenic *Arabidopsis* lines which express AtHb2 in comparison with the control. The individual measurements were carried out on in each case 5-10 seeds, and the corresponding oil contents are shown as µg fatty acids per seed.

| Line | WT | Line 10 | Line 9 | Line 11 | Line 2 |
|---|---|---|---|---|---|
|  | 6.39 | 8.36 | 9.79 | 8.26 | 8.73 |
|  | 9.38 | 8.53 | 8.50 | 9.66 | 8.36 |
|  | 9.38 | 9.83 | 9.79 | 8.23 | 9.11 |
|  | 7.48 | 9.72 | 9.93 | 8.98 | 8.57 |
|  | 9.38 |  | 6.69 | 11.16 |  |
|  | 6.87 |  | 3.06 |  |  |
|  | 8.44 |  | 7.54 |  |  |
|  | 6.03 |  |  |  |  |
|  | 3.93 |  |  |  |  |
| Mean | 7.48 | 9.11 | 7.90 | 9.26 | 8.69 |
| Standard deviation | 1.77 | 0.67 | 2.29 | 1.09 | 0.27 |
| Relative oil gain |  | 21.86 | 5.64 | 23.80 | 16.25 |

TABLE 6

Determination of the specific gravity of a transgenic line in comparison with a control plant.

|  | Wild type | | | | LegHb | | | |
| --- | --- | --- | --- | --- | --- | --- | --- | --- |
|  | Air | Water | Water/Air | Sp. grav. | Air | Water | Water/Air | Sp. grav. |
| Tuber 1 | 5.4500 | 0.2700 | 0.0500 | 1.0521 | 13.990 | 1.0000 | 0.0710 | 1.0770 |
| Tuber 2 | 8.9900 | 0.3300 | 0.0370 | 1.0381 | 15.530 | 1.1000 | 0.0710 | 1.0762 |
| Tuber 3 | 25.7900 | 1.4700 | 0.0570 | 1.0604 | 30.280 | 2.2000 | 0.0730 | 1.0783 |
| Tuber 4 | 30.7000 | 1.9300 | 0.0630 | 1.0671 | 50.740 | 3.2300 | 0.0640 | 1.0680 |
| Tuber 5 | 37.4500 | 1.9900 | 0.0530 | 1.0561 | 59.430 | 4.0600 | 0.0680 | 1.0733 |
| Tuber 6 | 80.9300 | 4.5000 | 0.0560 | 1.0589 | 67.120 | 4.3600 | 0.0650 | 1.0695 |
| Mean |  |  |  | 1.0555 |  |  |  | 1.0737 |
| STD |  |  |  | 0.0090 |  |  |  | 0.0039 |
| % Starch | 8.9181 |  |  |  | 12.554 |  |  |  |
| Increase in % |  |  |  |  | 40.77 |  |  |  |

We claim:

1. A method for increasing the production of starch and/or oil, comprising selecting a transformed plant that has an increase in starch and/or oil content as compared with a wild-type control plant, growing said transformed plant, and recovering the starch and/or oil from said transformed plant, wherein the transformed plant overexpresses at least one hemoglobin, and the overexpression of the at least one hemoglobin results in the increase in starch and/or oil content in the transformed plant as compared with the wild-type control plant.

2. The method of claim 1, wherein the at least one hemoglobin is from a plant selected from the group consisting of *Lupinus luteus, Glycine max, Medicago sativa, Medicago trunculata, Phaseolus vulgaris, Vicia faba, Pisum sativum, Vigna unguiculata, Lotus japonicus, Psophocarpus tetragonolobus, Sesbania rostrata, Casuarina glauca, Canvalaria lineate, Physcomitrella patens, Arabidopsis thaliana, Gossypium hirsutum, Oryza sativa, Brassica napus, Lycopersicon esculentum, Hordeum vulgare, Zea mays, Trema tomentosa,* and *Parasponia rigida.*

3. The method of claim 1, wherein the at least one hemoglobin is from *Arabidopsis thaliana.*

4. The method of claim 1, wherein the at least one hemoglobin is overexpressed in a storage-organ-specific manner.

5. The method of claim 1, wherein the at least one hemoglobin is overexpressed in a tuber-specific, seed-specific, or tuber- and seed-specific manner.

6. The method of claim 1, wherein the at least one hemoglobin is encoded by a nucleotide sequence having at least 95% identity with the nucleotide sequence as set forth in SEQ ID NO: 5 and the transformed plant has an increase in starch and/or oil content as compared with the wild-type control plant.

7. The method of claim 1, wherein the at least one hemoglobin is encoded by the nucleotide sequence as set forth in SEQ ID NO: 5.

8. The method of claim 1, wherein the transformed plant is a monocotyledonous crop plant.

9. The method of claim 1, wherein the transformed plant is a Gramineae species.

10. The method of claim 1, wherein the transformed plant is a dicotyledonous crop plant.

11. The method of claim 1, wherein the transformed plant is a Asteraceae, Brassicacea, Compositae, Cruciferae, Cucurbitaceae, Leguminosae, Rubiaceae, Solanaceae, Sterculiaceae, Theaceae or Umbelliferae species.

12. The method of claim 1, wherein the transformed plant is selected from the group consisting of *Borago officinalis* (borage), *Brassica campestris*, *Brassica napus*, *Brassica rapa* (mustard or oilseed rape), *Cannabis sativa* (hemp), *Carthamus tinctorius* (safflower), *Cocos nucifera* (coconut), *Crambe abyssinica* (crambe), *Cuphea* species, *Elaeis guinensis* (African oil palm), *Elaeis oleifera* (American oil palm), *Glycine max* (soybean), *Gossypium hirsutum* (American cotton), *Gossypium barbadense* (Egyptian cotton), *Gossypium herbaceum* (Asian cotton), *Helianthus annuus* (sunflower), *Linum usitatissimum* (linseed or flax), *Oenothera biennis* (evening primrose), *Olea europea* (olive), *Oryza sativa* (rice), *Ricinus communis* (castor-oil plant), *Sesamum indicum* (sesame), *Triticum* species (wheat), *Zea mays* (maize), walnut and almond.

13. The method of claim 1, wherein the transformed plant is potato, *Arabidopsis thaliana*, soybean or oilseed rape.

14. The method of claim 1, wherein the transformed plant is a T2 plant.

15. A method of achieving a better utilization of areas under cultivation or a better utilization of fertilizer, comprising selecting transformed plants that have an increased storage reserve content in storage organs as compared with a wild-type control plant in an area, and growing said transformed plants, wherein the transformed plants overexpress at least one hemoglobin and the overexpression of the at least one hemoglobin increases the storage reserve content in the storage organs of the transformed plants as compared with the wild-type control plant.

16. The method of claim 1, wherein the overexpression of the at least one hemoglobin results in an increase in starch content in the transformed plant as compared with the wild-type control plant.

17. A method for increasing the production of oil, comprising selecting a transformed plant that has an increase in oil content in seeds as compared with a wild-type control plant, growing said transformed plant, and recovering the oil from the seeds of said transformed plant, wherein the transformed plant overexpresses at least one hemoglobin, and the overexpression of the at least one hemoglobin results in the increase in oil content in the seeds of the transformed plant as compared with the wild-type control plant.

18. The method of claim 17, wherein the at least one hemoglobin is from a plant selected from the group consisting of *Arabidopsis thaliana*, *Lupinus luteus*, *Glycine max*, *Medicago sativa*, *Medicago trunculata*, *Phaseolus vulgaris*, *Vicia faba*, *Pisum sativum*, *Vigna unguiculata*, *Lotus japonicus*, *Psophocarpus tetragonolobus*, *Sesbania rostrata*, *Casuarina glauca*, *Canvalaria lineate*, *Physcomitrella patens*, *Arabidopsis thaliana*, *Gossypium hirsutum*, *Oryza sativa*, *Brassica napus*, *Lycopersicon esculentum*, *Hordeum vulgare*, *Zea mays*, *Trema tomentosa*, and *Parasponia rigida*.

19. The method of claim 17, wherein the at least one hemoglobin is encoded by the nucleotide sequence as set forth in SEQ ID NO: 5 or a nucleotide sequence having at least 95% identity with the nucleotide sequence as set forth in SEQ ID NO: 5 and the transformed plant has an increase in oil content as compared with the wild-type control plant.

20. The method of claim 17, wherein the transformed plant is a monocotyledonous crop plant or a dicotyledonous crop plant.

21. The method of claim 17, wherein the transformed plant is a Asteraceae, Brassicacea, Compositae, Cruciferae, Cucurbitaceae, Gramineae, Leguminosae, Rubiaceae, Solanaceae, Sterculiaceae, Theaceae or Umbelliferae species.

22. The method of claim 17, wherein the transformed plant is selected from the group consisting of *Arabidopsis thaliana*, *Borago officinalis* (borage), *Brassica campestris*, *Brassica napus*, *Brassica raga* (mustard or oilseed rape), *Cannabis sativa* (hemp), *Carthamus tinctorius* (safflower), *Cocos nucifera* (coconut), *Crambe abyssinica* (crambe), *Cuphea* species, *Elaeis guinensis* (African oil palm), *Elaeis oleifera* (American oil palm), *Glycine max* (soybean), *Gossypium hirsutum* (American cotton), *Gossypium barbadense* (Egyptian cotton), *Gossypium herbaceum* (Asian cotton), *Helianthus annuus* (sunflower), *Linum usitatissimum* (linseed or flax), *Oenothera biennis* (evening primrose), *Olea europea* (olive), *Oryza sativa* (rice), *Ricinus communis* (castor-oil plant), *Sesamum indicum* (sesame), *Triticum* species (wheat), *Zea mays* (maize), potato, walnut and almond.

23. A method for increasing starch and/or oil content in a plant, comprising transforming at least one hemoglobin into a plant, overexpressing said at least one hemoglobin in the plant, comparing starch and/or oil content of the plant with a wild-type control plant, and selecting a transformed plant with increased starch and/or oil content as compared with the wild-type control plant, wherein the overexpression of the at least one hemoglobin results in the increase in starch and/or oil content in said transformed plant as compared with the wild-type control plant.

24. The method of claim 23, wherein the at least one hemoglobin is from a plant selected from the group consisting of *Arabidopsis thaliana*, *Lupinus luteus*, *Glycine max*, *Medicago sativa*, *Medicago trunculata*, *Phaseolus vulgaris*, *Vicia faba*, *Pisum sativum*, *Vigna unguiculata*, *Lotus japonicus*, *Psophocarpus tetragonolobus*, *Sesbania rostrata*, *Casuarina glauca*, *Canvalaria lineate*, *Physcomitrella patens*, *Arabidopsis thaliana*, *Gossypium hirsutum*, *Oryza sativa*, *Brassica napus*, *Lycopersicon esculentum*, *Hordeum vulgare*, *Zea mays*, *Trema tomentosa*, and *Parasponia rigida*.

25. The method of claim 23, wherein the at least one hemoglobin is overexpressed in a storage-organ-specific manner.

26. The method of claim 23, wherein the at least one hemoglobin is overexpressed in tuber-specific, seed-specific, or tuber- and seed-specific manner.

27. The method of claim 23, wherein the hemoglobin is encoded by the nucleotide sequence as set forth in SEQ ID NO: 5 or a nucleotide sequence having at least 95% identity with the nucleotide sequence as set forth in SEQ ID NO: 5 and the transformed plant has an increase in starch and/or oil content as compared with the wild-type control plant.

28. The method of claim 23, wherein the transformed plant is a monocotyledonous crop plant or a dicotyledonous crop plant.

29. The method of claim 23, wherein the transformed plant is a Asteraceae, Brassicacea, Compositae, Cruciferae, Cucurbitaceae, Gramineae, Leguminosae, Rubiaceae, Solanaceae, Sterculiaceae, Theaceae or Umbelliferae species.

30. The method of claim 23, wherein the transformed plant is selected from the group consisting of *Arabidopsis thaliana, Borago officinalis* (borage), *Brassica campestris, Brassica napus, Brassica rapa* (mustard or oilseed rape), *Cannabis sativa* (hemp), *Carthamus tinctorius* (safflower), *Cocos nucifera* (coconut), *Crambe abyssinica* (crambe), *Cuphea* species, *Elaeis guinensis* (African oil palm), *Elaeis oleifera* (American oil palm), *Glycine max* (soybean), *Gossypium hirsutum* (American cotton), *Gossypium barbadense* (Egyptian cotton), *Gossypium herbaceum* (Asian cotton), *Helianthus annuus* (sunflower), *Linum usitatissimum* (linseed or flax), *Oenothera biennis* (evening primrose), *Olea europea* (olive), *Oryza sativa* (rice), *Ricinus communis* (castor-oil plant), *Sesamum indicum* (sesame), *Triticum* species (wheat), *Zea mays* (maize), potato, walnut and almond.

31. The method of claim 1, wherein the overexpression of the at least one hemoglobin results in an increase in starch and oil content in the transformed plant as compared with the wild-type control plant.

* * * * *